United States Patent [19]

Vander Jagt et al.

[11] Patent Number: 4,806,568
[45] Date of Patent: Feb. 21, 1989

[54] GOSSYPOL DERIVATIVES

[75] Inventors: David L. Vander Jagt, Albuquerque; Robert E. Royer, Bosque Farms, both of N. Mex.

[73] Assignee: Research Corporation, New York, N.Y.

[21] Appl. No.: 775,196

[22] Filed: Sep. 12, 1985

[51] Int. Cl.⁴ .................. C07C 121/64; A61K 31/275
[52] U.S. Cl. ..................................... 514/522; 558/414
[58] Field of Search .......................... 558/414; 514/522

[56] References Cited

U.S. PATENT DOCUMENTS 4,297,341 10/1981 Waller et al. .......................... 424/80
4,381,298 4/1983 Coulson .............................. 424/240

OTHER PUBLICATIONS

Vander Jagt et al, "Chem Abs.," vol. 102, (1985)102:42729z.
Manmade, A., et al., "Experientia", vol. 39 (1983) pp. 1276–1277.
Dorsett, P. H., et al., "J. Pharm. Sci.", vol. 64 (1975), pp. 1073–1075.
Montomat, E. E., et al. "Science", vol. 218 (1982) pp. 288–289.
Heidrich, J. E. et al. "IRCS Med. Sci.", vol. 11 (1983) p. 304.
Clark, E. P., "J. Biol. Chem.", vol. 75 (1927), pp. 725–739.
Nat'l. Coordinating Group on Male Antifertility Agents, "Chinese Med. J.", vol. 4 (1978), pp. 417–428.
Royer, R. E., "FEBS", vol. 157 (1983), pp. 28–30.
Vander Jagt, D. L., et al. "J. Biol. Chem.", vol. 258 (1983), pp. 5689–5694.
Vander Jagt, D. L., et al., "IRCS Med. Sci.", vol. 12 (1984), pp. 845–846.

Primary Examiner—Anton H. Sutto
Attorney, Agent, or Firm—Scully, Scott, Murphy & Presser

[57] ABSTRACT

This invention relates to a compound of the formula:

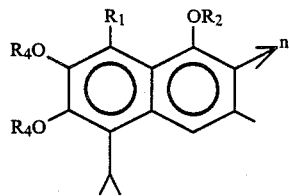

wherein
  $R_1$ is C≡N or $COR_3$; and $R_2$ is alkyl, alkenyl, alkynyl, or acyl wherein
  $R_3$ is hydrogen, alkyl, alkenyl, alkynyl, hydroxy, amino or alkoxy
  $R_4$ is hydrogen, alkyl or acyl; and
  n is the integer 1 or 2.

10 Claims, No Drawings

GOSSYPOL DERIVATIVES

The invention described herein was made in the course of work under a grant sponsored in part by the National Institutes of Health and the Department of Health and Human Services.

FIELD OF THE INVENTION

The present invention relates to derivatives of the compound gossypol and hemigossypol. In particular, the invention relates to gossypol derivatives useful in the treatment of malaria and viral disease.

BACKGROUND OF THE INVENTION

The compound gossypol is a polyphenolic triterpene having the formula:

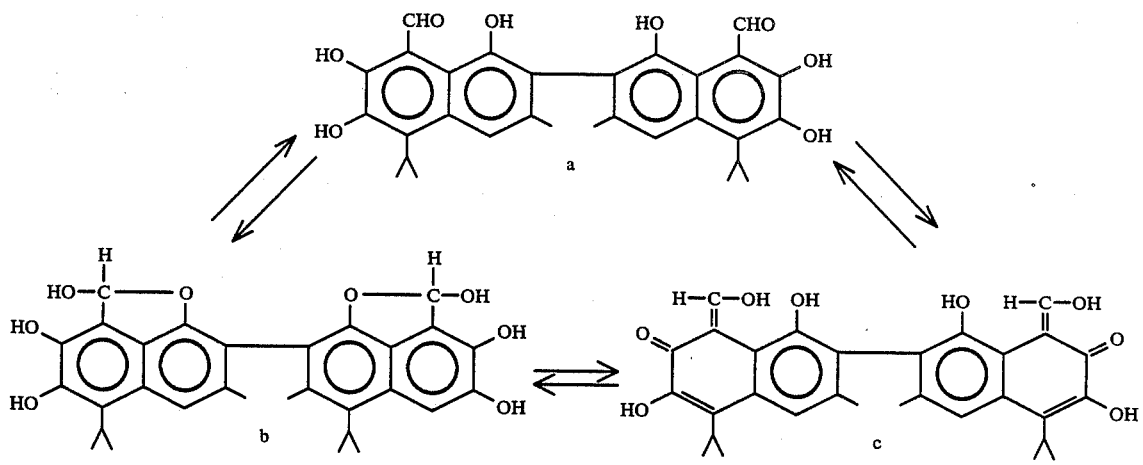

wherein b and c are tautomers of the aldehyde a. Gossypol exists primarily as the aldehyde form in nonpolar solvents and is represented as such throughout the specification and claims.

The substance is found in certain types of cotton plants, and is the main toxic material found therein. As such, it has limited the use of cottonseed meal as a source of dietary protein for monogastric animals including man. Gossypol has, however, exhibited a number of useful biological properties which have aroused great interest in the compound among medical researchers.

For example, gossypol has been under investigation in China, based on the discovery that the use of cottonseed oil in cooking induced infertility in men (Nat'l. Coordinating Groups on Male Fertility, *Chinese Med. J.* 4: 417–428, 1978). This feature of its activity has been used to attempt to produce a male contraceptive using gossypol as the active agent (U.S. Pat. No. 4,381,298) and also a vaginal spermicide (U.S. Pat. No. 4,297,341). Similar properties have been attributed to the compound hemigossypol. (Manmade, et al., *Experiencia* 39, 1276). It has further been shown to have antiviral properties, being capable of inactivating parainfluenza, type 3 and herpes simplex viruses (Dorsett et al., *J. Pharm. Sci.* 64, 1073, 1975). Antiparasitic activity has also been found to be associated with gossypol. Growth of both *Trypanosoma cruzi* (Montamat et al., *Science* 218, 218, 1982) and *Plasmodium falciparum* (Heidrich et al., *IRCS Med. Sci.* 11, 304, 1983) is known to be inhibited by gossypol Overall, however, the practical application of these important properties has been prevented by the toxicity and unpleasant side effects produced by gossypol.

A considerable body of research indicates that the toxicity of gossypol is related to the reactions of the aldehyde groups on the molecule. It should thus be theoretically possible to remove the aldehyde groups from a gossypol molecule and reduce the toxicity. However, it is unclear at present how much of gossypol's biological activity is also tied to the presence of the reactive aldehyde groups. Therefore, it is impossible to know in advance whether the gossypol molecule without the aldehydes would exhibit the same activity as the natural molecules. It is also completely unpredictable as to what, if any, substituent groups might be used as an appropriate replacement for the aldehyde groups, and which might aid in allowing the new compound to mimic the biological activity of the original compound.

It has now been unexpectedly discovered that a new class of compounds, derived from gossypol, or hemigossypol, succeed in retaining a similar, and sometimes higher, level of activity than the parent compound, while being free of the toxic aldehyde groups. Such compounds are shown herein, like gossypol itself, to exhibit significant levels of biological activity with significantly reduced toxicity. Further, an additional new class of compounds has been prepared which serve as useful intermediates in the preparation of the biologically active compounds of the present invention.

BRIEF DESCRIPTION OF THE INVENTION

The present invention provides compounds of the formula

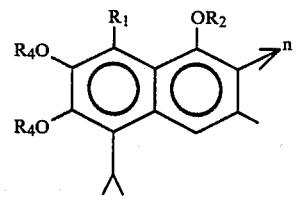

wherein
$R_1$ is C≡N or $COR_3$; and $R_2$ is alkyl, alkenyl, alkynyl or acyl;
wherein
$R_3$ is hydrogen, alkyl, alkenyl, alkynyl, hydroxy, amino, or alkoxy;

$R_4$ is hydrogen, alkyl or acyl; and n is the integer 1 or 2.

The series of compounds wherein n is 1 are derivatives of hemigossypol These compounds can be made by reactions similar to those used for preparing derivatives of gossypol where n is 2. The only significant difference in preparation is whether gossypol or hemigossypol is used as the starting material, as the preparative methods are otherwise identical in all respects.

The present invention also provides intermediates of the formula:

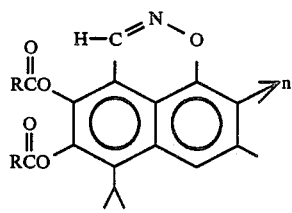

wherein R is alkyl which are useful in the preparation of some of the biologically active compounds of the present invention.

DETAILED DESCRIPTION OF THE INVENTION

The compounds of the present invention are gossypol or hemigossypol derivatives in which the aldehyde groups of the gossypol or hemigossypol molecule have been removed, effecting a reduction in toxicity. Surprisingly, the derivative compounds retain a high level of biological activity in spite of the removal of the reactive aldehyde groups. The present compounds have shown specific utility in the treatment of malaria and viruses, however, it is also contemplated that they be used as spermicides, contraceptives, and antiparasitic agents, as is the parent compound gossypol.

In the present compounds, the alkyl, alkenyl, alkynyl aryl and alkoxy and substituents preferably contain 1–6 carbon atoms. Throughout this application, and in the claims, amino is intended to include substituted amino, wherein their substituent may be alkyl, alkenyl, alkynyl, alkoxy and acyloxy. The preferred compounds of the present invention are those in which $R_1$ is C≡N, i.e., the nitriles. Particularly preferred among the present compounds is gossylic nitrile diacylate. The preferred acyl substituents are acetate, propionate and butyrate.

The compounds of the present invention may be prepared by variations on a single synthetic pathway. Critical in the preparation of the compounds are a family of key intermediates, themselves new compounds, gossypol dianhydrooxime tetraacylates. Particularly preferred is gossypol dianhydrooxime tetraacetate. These compounds may be used to prepare a wide variety of derivatives in the gossylic nitrile family, from which further derivatives may be prepared. The procedure for synthesis of these important intermediates is described representatively in Example 1. This family of compounds can be prepared readily, by treatment of the known compound, gossypol dioxime, with the appropriate acid anhydride, followed by addition of the corresponding acid salt at high temperature to yield the desired dianhydro- oxime tetraacylate.

To form the substituted nitriles of the present invention, gossypol-dianhydro-oxime tetraacylate is treated with an electrophile and a base to simultaneously form the nitriles, and selectively acylate or alkylate the perihydroxyls. The conversion of the intermediate compounds to a nitrile involves the elimination of a phenol, and its trapping by the electrophile. The substituents will of course depend upon the electrophile used. For example, the use of acetic anhydride will produce compounds with acetyl groups on the perihydroxyls. Alternately, a disubstituted alkyl sulfate may be used as the electrophile to produce 1,1-dimethyl gossylic nitrile. Appropriately substituted carboxylic acid anhydrides and carboxylic acid salts may also be employed in converting the dioximes to the nitrile compounds.

From a nitrile compound in which $R_2$ is alkyl, a number of additional gossypol derivatives may be prepared. Acid hydrolysis of the nitrile compounds can lead to amides, esters, or carboxylic acids depending upon the conditions employed. A general, exemplary scheme for the preparation of these compounds proceeds as follows:

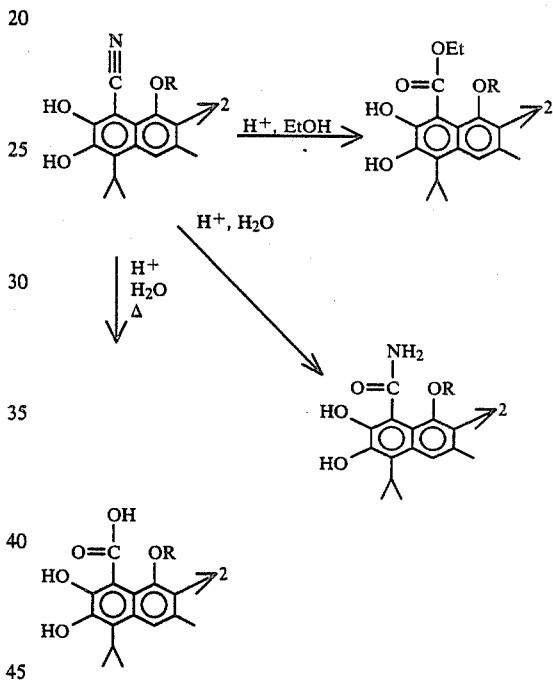

As noted above, the compounds of the present invention demonstrate significant antimalarial and antiviral activity while at the same time showing very low levels of toxicity. Concentrations of gossylic nitrile diacetate, for example, have been shown to effectively inhibit growth of *Plasmodium falciparum* in a amounts as low as $10^{-4}$M. Gossylic nitrile dipropionate and dibutyrate are effective at even lower concentrations. Similarly, the present derivatives also show significant levels of antiviral activity (Example 4). Although in some circumstances, some of the derivatives may show slightly lesser levels of activity than the parent compound gossypol, this is more than adequately compensated for by the fact that all the tested derivatives are far less toxic than gossypol, and therefore may be used at much higher levels with no ill effects In fact, the toxicity of gossypol is so high, even at very low levels, that it has found virtually no widely accepted practical pharmaceutical application for any purpose. Therefore, the present derivatives, in practice, appear to have essentially all the advantages, yet none of the disadvantages, of the parent compound.

For use as therapeutic agents, the present compounds may be used alone, or in combination with a variety of pharmaceutically acceptable carriers.

The compounds of this invention are thus useful as antimalarial and antiviral agents in mammals when administered in amounts ranging from about 0.5 to about 50 mg per day, depending on route of administration. This dosage regimen may be adjusted to provide the optimum therapeutic response, depending upon the condition being treated. For example, several divided doses may be administered daily for the dose may be proportionally reduced as indicated by the exigencies of the therapeutic situation. A decided practical advantage is that the active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compounds may also be administered parenterally or intraperitoneally. Solutions of the active compound as a free acid or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersosal, and the like. In many cases, it will be preferable to include isotonic agents, for example sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compostions.

It is essentially advantageous to formulate parental compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieves, and (b) the limitations inherent in the art of compounding such an active material for the treatment of disease in living subject having a diseased condition in which bodily health is impaired as herein disclosed in detail The present invention may be better understood with reference to the following non-limiting examples.

EXAMPLE 1

The following represents the process for preparation of the intermediate compound gossypol dianhydrooxime tetraacetate and the biologically active compound gossylic nitrile diacetatate.

A suspension of gossypoldioxime (Clark, *J. Biol, Chem.* 75: 725,1927) in acetic anhydride was stirred at room temperature for six hours to give a yellow intermediate. The NMR spectrum has a single new peak ($\sigma$=2.23), corresponding to a pair of chemically equivalent acetyl groups. Since the phenolic hydroxyls of gossypol are not acetylated under conditions used, the yellow intermediate is understood to be the acetylated oxime.

Treatment of the resulting oxime, still in acetic anhydride, with sodium acetate on a boiling water bath for about 30 minutes gave the dianhydro-oxime tetraacetate. The NMR spectrum of this compound indicates the presence of two pairs of equivalent acetyl groups and no free hydroxyls. The aldehyde proton signal of gossypol ($\sigma$=11.18) is replaced by one for the benzylimino proton ($\sigma$=8.90).

The dianhydro-oxime tetraacetate was converted directly to gossylic nitrile hexaacetate by bringing the reaction mixture to a boil for a short period of time. The formation of the nitrile functionality was clearly indicated in the IR spectrum by a band at 2230 cm$^{-1}$. The NMR spectrum of this compound has signals for three pairs of equivalent acetyl groups, a singlet at $\sigma$=2.28 (6H) and a singlet at $\sigma$=2.48 (12H). The downfield signal was assigned to the acetyl groups on the ortho phenols which have similar chemical environments. The benzylimino proton signal had disappeared and there were no signals for free hydroxyl groups.

The four groups protecting the ortho hydroxyls of the latter compound were easily removed with sodium bicarbonate in refluxing aqueous methanol to give gossylic nitrile diacetate. The presence of the nitrile function in this compound is apparent from a band in the IR at 2220 cm$^{-1}$ and the presence of the acetyl function by a band at 1765 cm$^{-1}$. The NMR spectrum has a signal at $\sigma$=2.24 corresponding to one pair of chemically equivalent acetyl groups and a broad peak at $\sigma$=6.4 corresponding to four free hydroxyl groups. The close correspondence of the signal at 2.24 to the upfield acetyl signal in the NMR spectrum of gossylic nitrile hexaacetate indicates that the pair of acetyl groups in gossylic nitrite diacetate are peri to the nitriles. These acetyl groups were unaffected by base. Acid hydrolysis resulted in destruction of the nitrile function and production of an intractable mixture. The resistance of the acetyl groups to basic hydrolysis further confirms that they are peri to the nitriles. It has been shown that a similarly crowded ester was resistant to saponification. Although the nitrile hexaacetate formed readily from the dianhydro-oxime in the presence of acetic anhydride, the dianhydro-oxime tetraacetate was not affected by sodium acetate in inert solvents or by sodium hydride in toluene, even at reflux. This indicates that the nitrile function might not be stable in the presence of a free peri hydroxyl.

The conversion of dianhydrooxime to gossylic nitrile requires the presence of the electrophile, acetic anhydride, to trap the phenolate oxygen as it is formed. Other electrophiles will work in the same way to convent key intermediate dianhydrooxime tetraacetate to a series of gossylic nitriles with different peri substituents, although there might be steric constraints on the choice of electrophile.

EXAMPLE 2

The following example provides additional information of the physical properties of the compound described in Example 1:

In the following experiments, melting points were determined on a VWR Scientific Electrothermal capillary melting point apparatus and are uncorrected. Infrared spectra were obtained on a Beckman IR-33 spectrophotometer in KBr pellets. The $^1$H NMR spectra were taken with a Varian FT 80-A (80 MHz) spectrometer and chemical shifts are reported in units downfield from Me$_4$Si. The samples were prepared as 10% solutions by weight in CDCl$_3$. The residual CHCl$_3$ signal was used as an internal standard. The gossypol acetic acid used in this research was provided by the Southern Regional Research Center of the USDA. Solvents and other chemicals were reagent grade. Gossypol dioxime was prepared by heating gossypol with neutralized hydroxyamine hydrochloride in ethanol according to the method of Clark (ibid.).

Gossypol dianhydrooxime tetraacetate: One gram (1.8 mmol) of the white gossypol dioxime was stirred in 5 ml of acetic anhydride for 5 hours at room temperature. One gram of freshly fused and powdered sodium acetate was added to the light yellow suspension and stirring was continued for two more hours. The reaction flask was then placed in a water bath which was slowly heated to boiling over a period of 30 min. and held at boiling for an additional 30 min. The reaction mixture was allowed to cool, poured onto 50 g of ice and stirred until the acetic anhydride was hydrolyzed. The light yellow crude product was filtered off, washed with water, and recrystallized from methanol/acetone to give 800 mg (1.18 mmol, 65%) of white microcrystalline plates mp 210°-215° C.; NMR 1.61 (d, 12 H, J=7 Hz), 2.05 (s, 6 H), 2.36 (s, 6 H), 2.59 (s, 6 H), 4.02 (m, 2 H, J=Hz), 8.21 (s, 6 H); 8.90 (s, 2 H); IR 2980, 2945, 2880, 1775, 1590, 1515, 1455, 1430, 1370, 1340, 1255, 1175, 1120, 1090, 1015, 910, 870. Anal. Calcd. for C$_{38}$H$_{36}$N$_2$O$_{10}$: C, 67.05; H, 5.33; N, 4.11. Found: C, 66.83; H, 5.63; N, 4.17.

Gossylic nitrile hexaacetate: the previous compound was prepared as described above, but was not isolated. Instead the reaction flask was taken off the boiling water bath, placed on a hot plate and brought to a slow boil for 30 min. The reaction mixture was then cooled and hydrolyzed on 50 g of ice. The product was filtered, washed with water, and recrystallized from methanol/acetone to give 980 mg (1.28 mmol, 71%) of white, microcrystalline material: mp 281°-284° C.; NMR 1.52 (d, 12 H, J=7 Hz), 2.08 (s, 6 H), 2.28 (s, 6 H), 2.48 (s, 12 H), 3.85 (Sept, 2 H), 8.13 (s, 2 H) IR 2980, 2940, 2885, 2230, 1780, 1620, 1420, 1365, 1180, 1135, 1025, 900, 860. Anal. Calcd. for C$_{42}$H$_{40}$N$_2$O$_{12}$: C, 65.96; H, 5.27; N, 3.66. Found: C, 66.05; H, 5.56; N, 3.61.

Gossylic nitrile diacetate: Nitrile hexaacetate (500 mg, 0.65 mmol) was added to 5 mL of methanol. One mL of water and 500 mg of sodium bicarbonate were added and the mixture was refluxed for 30 min. The mixture was allowed to cool and was acidified by dropwise addition of acetic acid. Ten mL of water was added, and the reaction mixture was chilled. The off-white product was filtered, washed with water and dried. It was recrystallized once from methanol/water and once from toluene/acetone to give 275 mg (0.46 mmol, 71%) of microcrystalline needles: mp 300°-302° C., decomp.; NMR 1.58 (d, 12 H, J=7 Hz), 1.98 (s, 6 H), 2.24 (s, 6 H), 3.96 (Sept, 2 H, J=7 Hz), 6.4 (s, 4 H, Broad), 7.98 (s, 2 H); IR 3450, 2980, 2940, 2885, 2220, 1765, 1610, 1450, 1370, 1340, 1290, 1185, 1110, 1025, 865, 750. Anal. Calcd. for $C_{34}H_{32}N_2O_8$: C, 68.45; H, 5.41; N, 4.70. Found C, 68.36; H, 5.73; N, 4.43.

2a

Following the procedure for synthesis of gossypol dianhydro-oxime tetraacetate in Example 1, but substituting propionic anhydride and sodium propionate for acetic anhydride and sodium acetate, gossypol dianhydro-oxime tetrapropionate and gossylic nitrile dipropionate were prepared. Following the analytical procedures described above, the final compound decomposed without melting IR peaks were at 3420, 2960, 2940, 2880, 2220, 1770, 1670, 1625, 1450, 1350, 1250, 1175, 1125, and 1075 $cm^{-1}$. The sharp peak at 2220 shows the presence of the nitrile function, and the peak at 1770 shows the presence of the carboxylate ester.

Similarly, replacing acetic anhydride and sodium acetate with butyric anhydride and sodium butyrate, respectively, gossypol dianhydro-oxime tetrabutyrate and gossylic nitrile dibutyrate were also prepared. The final compound melted at 155°-160° C., with decomposition. IR peaks were at 3420, 2990, 2960, 2900, 2245, 1775, 1650, 1460, 1390, 1360, 1300, 1250, 1175, 1140, and 1100 $cm^{-1}$. The presence of the nitrile function is shown by the sharp peak at 2245 and the presence of the carboxylate ester is shown by the peak at 1775.

In each of the above cases, it was possible, but not necessary, to isolate the intermediate compounds.

EXAMPLE 3

This Example is intended to demonstrate the decrease in toxicity observed in some gossypol derivatives.

Vero cells, a monkey kidney-derived cell liner, were grown in petri dishes. In culture these cells exhibit monolayer formation. The cytopathology of the drugs is determined by examining the cell monolayer for abnormal cell morphology.

Drugs at different concentration in a solution of DMSO were added to culture dishes at the same time cells were added. Controls contained no added drug, but contained equivalent amounts of DMSO. After 24-48 hours, monolayers were examined for abnormal cell morphology.

Table 1 shows the results of the toxicity tests. The designation "−" indicates no detectable toxicity; "+" indicates low but detectable toxicity; "++" indicates marked toxicity.

TABLE 1

| Drug | Concentration | | |
|---|---|---|---|
| | 5 uM | 10 uM | 50 uM |
| gossypol | + | ++ | ++ |
| gossylic nitrile diacetate | − | − | + |
| gossylic nitrile dipropionate | − | − | ++ |
| gossylic nitrile dibutyrate | − | − | ++ |

The above data show conclusively that the present gossypol derivatives are significantly less toxic than the parent compound gossypol. Gossylic nitrile diacetate shows particularly low levels of toxicity, approximately 10 times less toxic than gossypol. The remaining two derivatives are approximately 5 times less toxic than gossypol.

EXAMPLE 4

The following data show the antiviral activity of various gossylic nitrile diacylates:

Gossypol, gossylic nitrile diacetate, gossylic nitrile dipropionate and gossylic nitrile dibutyrate were all tested for their action against herpes simplex virus, specifically herpes simplex II. Vero cells, a monkey kidney derived cell line was used as the host cell. Virus growth in all tests was monitored by following cytopathic changes in the cell monolayer.

A. These results show the effect of pretreatment of virus with the drugs.

Each drug was added to virus for 30 minutes without serum present, after which serum was added, and the resulting mixture was layered onto a monolayer of vero cells. Controls contained DMSO at the same concentration present in the drug studies. Results are shown in Table 2. The concentrations shown are concentrations used for the initial 30 minute treatment of the virus.

In Table 2 and those to follow, T represents a toxic effect so pronounced that antiviral effects are masked. "½+" indicates good antiviral activity and "−" indicates no virus growth at all.

TABLE 2

| Drug | Concentration | | |
|---|---|---|---|
| | 5 uM | 10 uM | 50 uM |
| gossypol | T | T | T |
| gossylic nitrile diacetate | ½+ | ½+ | − |
| gossylic nitrile dipropionate | ½+ | ½+ | T |
| gossylic nitrile dibutyrate | − | − | T |

The above results indicate that gossylic nitrile dibutyrate has the best antiviral activity, while gossylic nitrile diacetate was least toxic. All derivatives showed good levels of activity, while generally being less toxic that gossypol.

B. This test shows the results of drug addition to cells already infected with virus.

Virus in Eagles MEM media without serum was added to the monolayer. After 30 minutes, 2% fetal calf serum was added. After a further 90 minute period, during which the virus was allowed to adsorb to and enter the cells, the drugs were added. Observations of viral growth under these circumstances showed that gossylic nitrile diacetate exhibited the most marked effect on virus in the infected cells, while gossypol's toxicity continued to mask any antiviral activity.

C. This test was designed to allow the demonstration of the effects of gossypol on antiviral activity without the mashing effects of its toxicity.

Each drug was added to virus without serum for 30 minutes as in A. The mixture was then diluted 5 times with Eagles MEM media without serum, and then added to a monolayer of viro cells for 30 minutes. The cells were then washed with Eagles MEM twice before new media plus serum were added. Thus, the drug is removed during the period after the virus enters the cell. The results are shown in Table 3 "+" indicates some level of virus growth; "n.d."=not determined; and "−" indicates no virus growth.

TABLE 3

| Drug | Concentration | | |
|---|---|---|---|
| | 5 uM | 10 uM | 50 uM |
| gossypol | ½+ | − | n.d. |
| gossylic nitrile diacetate | + | ½+ | − |

TABLE 3-continued

| Drug | Concentration | | |
|---|---|---|---|
| | 5 uM | 10 uM | 50 uM |
| gossylic nitrile dipropionate | n.d. | — | — |
| gossylic nitrile dibutyrate | + | ½+ | n.d. |

Under these test conditions, all the gossypol derivatives show good antiviral effects gossylic nitrile dipropionate exhibits effects essentially equivalent to those of gossypol.

EXAMPLE 5

This example shows the antimalarial activity of various gossylic nitrile diacylate compounds.

*Plasmodium falciparum* was grown in human erythrocytes in a 5% $CO_2$ 95% air mixture, in RPMI media with 10% rabbit serum. Drugs in DMSO (final concentration of DMSO 1%) were added, along with $^3H$-hypoxanthine, to ring stage parasites at an initial parasitemia of about 0.1%. Control cultures received DMSO and $^3H$-hypoxanthine. Cultures were incubated for 3 days at 37° C., which allowed for maturation of the parasites, reinvasion, and a second round of maturation. The cells were harvested on filters and counted by liquid scintillation spectrometry.

Table 4 shows results obtained to demonstrate the effectiveness of the gossylic nitrile diacylate derivatives in preventing parasite growth.

TABLE 4

| Drug | Concentration required to prevent growth |
|---|---|
| gossylic nitrile diacetate | 100 uM |
| gossylic nitrile dipropionate | 40 uM |
| gossylic nitrile dibutyrate | 40 uM |

These results show that all the derivatives tested have the ability to prevent parasite growth, with the diacetate derivatives being least effective. Although the three tested compounds are somewhat less potent than gossypol with respect to antimalarial activity, this is amply counterbalanced by the fact that they are far less toxic, as shown in Example 3.

What is claimed is:

1. A compound of the formula:

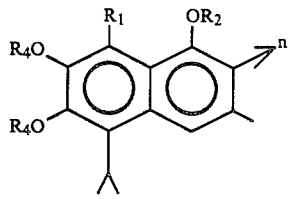

wherein
 $R_1$ is C≡N;
 and $R_2$ is $C_1$ to $C_6$ acyl;
 $R_4$ is hydrogen;
 and n is the integer 1 or 2.

2. The compounds of claim 1 wherein n is 2.
3. The compounds of claim 1 wherein $R_2$ is acetate.
4. The compounds of claim 1 wherein $R_2$ is propionate.
5. The compounds of claim 1 wherein $R_2$ is butyrate.
6. A therapeutic compositon comprising a compound of the formula

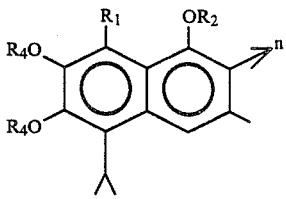

wherein
 $R_1$ is C≡N;
 and $R_2$ is $C_1$ to $C_6$ acyl;
 $R_4$ is hydrogen;
 and n is the integer 1 or 2; in combination with a pharmaceutically acceptable carrier.

7. The composition of claim 6 wherein n is 2.
8. The composition of claim 6 wherein $R_2$ is acetate.
9. The composition of claim 6 wherein $R_2$ is propionate.
10. The composition of claim 6 wherein $R_2$ is butyrate.

* * * * *